United States Patent [19]

Hara et al.

[11] Patent Number: 5,204,089
[45] Date of Patent: Apr. 20, 1993

[54] METHOD OF PREVENTING THE FORMATION OR AGGREVATION OF DENTAL PLAQUE AND METHOD FOR REDUCING CARIOGENESIS

[75] Inventors: Yukihiko Hara, Fujieda; Masao Hattori, Toyama, both of Japan

[73] Assignee: Mitsui Norin Co., Ltd., Tokyo, Japan

[21] Appl. No.: 836,158

[22] Filed: Feb. 13, 1992

Related U.S. Application Data

[63] Continuation of Ser. No. 547,639, Jul. 2, 1990, abandoned.

[30] Foreign Application Priority Data

Aug. 30, 1989 [JP] Japan .................. 1-221816

[51] Int. Cl.$^5$ .................. A61K 7/16; A61K 7/26; A61K 35/78
[52] U.S. Cl. .................. 424/58; 424/49; 424/195.1; 426/597
[58] Field of Search .................. 424/49-58, 424/195.1; 426/597

[56] References Cited

U.S. PATENT DOCUMENTS

| | | | |
|---|---|---|---|
| 4,613,672 | 9/1986 | Hara | 549/399 |
| 4,673,530 | 6/1987 | Hara | 252/398 |
| 4,840,966 | 6/1989 | Hara et al. | 514/456 |
| 4,906,480 | 3/1990 | Kashket | 426/3 |
| 4,913,909 | 4/1990 | Hara et al. | 424/688 |

OTHER PUBLICATIONS

Kashket et al C.A. 104:128611h (1986).
Sakanaka et al I C.A. 111:160278k (1989) of Jpn. 019012y Apr. 6, 1989.
Kawamura et al I, C.A. 111:150452y (1989).
Cao et al C.A. 111:187539h (1989).
Sakanaka et al II C.A. 11:193341d (1989).
Hatta et al C.A. 112:223164p (1990) of Jpn 01 265010 Oct. 23, 1989.
Hattori et al C.A. 113:55595e (1990).
Kawamura et al II C.A. 113:217824h (1990) of Jpn 02 25413 Jan. 26, 1990.
Sakanaka C.A. 114:220548x (1991).
Masao Hattori et al, "Effect of Tea Polyphenols on Glucan Synthesis by Glucosyltransferase from Streptococcus mutans" (1990), pp. 717-720, Chemical Pharmaceutical Bull. 38(3), vol. 38.
Masao Onisi, "The Feasibility of a Tea Drinking Program for Dental Public Health in Primary Schools", (Jul. 1985), pp. 134-143, The Journal of Dental Health, vol. 35, No. 3.
Chemical Abstracts, vol. 110:92316y, p. 437, 1989.
Chemical Abstracts, vol. 99:10705s, p. 295, 1983.
Chemical Abstracts, vol. 114:220548x, p. 2, 1991.
Chemical Abstracts, vol. 101:53375m, 1984.
Chemical Abstracts, vol. 101:53376n, 1984.
Chemical Abstracts, vol. 107:161418k, 1987.
Chemical Abstracts, vol. 110:141224c, 1989.
Chemical Abstracts, vol. 110:179296r, 1989.
Kashket et al, "In-Vitro Inhibition of Glucosyltransferase From the Dental Plaque Bacterium Streptococcus Mutans By Common Beverages and Food Extracts", Archs. Oral Biol, vol. 30, 11/12, pp. 821-826, 1985.

*Primary Examiner*—Shep K. Rose
*Attorney, Agent, or Firm*—Frishauf, Holtz, Goodman & Woodward

[57] ABSTRACT

An anti-dental plaque agent is composed primarily of a tea-leaf polyphenol or polyphenols selected from the group consisting of epigallocatechin gallate or its isomer, epicatechin gallate or its isomer, epigallocatechin or its isomer, epicatechin or its isomer, (+)catechin or its isomer, free type theaflavin, theaflavin monogallate A, theaflavin monogallate B and theaflavin digallate.

8 Claims, No Drawings

METHOD OF PREVENTING THE FORMATION OR AGGREVATION OF DENTAL PLAQUE AND METHOD FOR REDUCING CARIOGENESIS

This application is a continuation of application Ser. No. 07/547,639, filed Jul 2, 1990 now abandoned.

BACKGROUND OF THE INVENTION

The present invention relates to an anti-dental plaque agent and, more particularly, to an anti-dental plaque agent which inhibits the formation of water-insoluble glucan by glucosyltransferase (hereinafter often abbreviated as GTF) which *Streptococcus mutans* produces extracellularly.

Dental caries is an infectious disease of the hard tissue of teeth which has afflicted mankind from ancient times up to now and is spread all over the world.

Of pathogenic bacteria causing dental caries, *Streptococcus mutans* is a primary important cariogenic bacterium. Glucan that is a polymer of glucose is synthesized from sucrose by the action of glucosyltransferase which is produced extracellularly by the above pathogenic bacteria Water-insoluble glucan has the property of adhering firmly to a smooth tooth surface. This water-insoluble glucan and *Streptococcus mutans* adhering to the tooth surface through it continue to grow and eventually overspread the tooth surface This is called "a dental plaque". Making use of various sugars, *Streptococcus mutans* generates some acids inclusive of lactic acid in the dental plaque, which in turn decalcify enamel. At this time, water-insoluble glucan is considered to play a role in preventing the diffusion of the acids.

Thus, the primary action of *Streptococcus mutans* in cariogenesis is to form water-insoluble glucan by GTF.

Heretofore, various pharmaceuticals for inhibiting cariogenesis have been proposed However, there is still a strong demand toward developing a pharmaceutical preparation which is so harmless to the human body that it can be safe in use.

SUMMARY OF THE INVENTION

As a result of intensive and extensive studies made in search of a substance having the desired pharmaceutical effect from naturally occurring materials, rather than from chemically synthesized materials, it has now been found that said substance is contained in the components of tea leaves.

As hitherto known, tea is effective against preventing dental caries. However, its acting factor has been considered to be fluorine contained in tea, which enhances dentine *per se*, preventing it from being attacked by cariogenic bacteria and decalcified by acids.

The present inventor has now found that the effect of tea upon preventing cariogenesis is obtained by a material composed mainly of tea polyphenols which, separately from the action of fluorine, inhibit considerably the ability of GTF to produce water-insoluble glucan.

A principal component of tea is tea polyphenol compounds, and said tea polyphenol compounds include the tea catechin compounds represented by the general formula (I) given below and the theaflavin compounds represented by the general formula (II) given below, and also thearubigin:

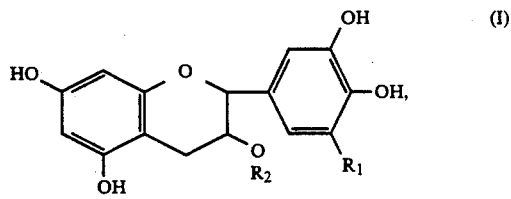

in which $R_1$ is a hydrogen atom or a hydroxy group and $R_2$ is a hydrogen atom or a 3,4,5-trihydroxy benzoyl group; and

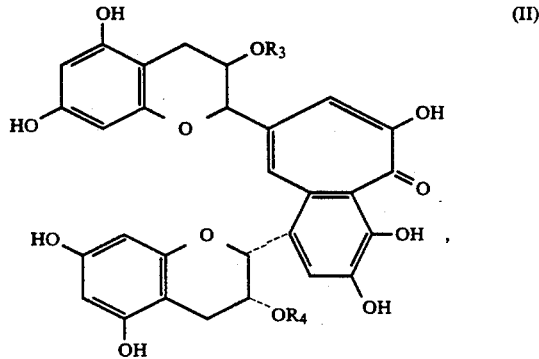

in which $R_3$ and $R_4$ are, each independently from the other, a hydrogen atom or a 3,4,5-trihydroxy benzoyl group Particular examples of the tea catechin compounds represented by the general formula (I) include (−)epicatechin, which is a compound of the formula (I) with $R_1=H$ and $R_2=H$; (−)epigallocatechin, which is a compound of the formula (I) with $R_1=OH$ and $R_2=H$; (−)epicatechin gallate, which is a compound of the formula (I) with $R_1=H$ and $R_2=3,4,5$-trihydroxy benzoyl group; and (−)epigallocatechin gallate, which is a compound of the formula (I) with $R_1=OH$ and $R_2=3,4,5$-trihydroxy benzoyl group. Particular examples of the theaflavin compounds include free theaflavin, which is a compound of the formula (II) with $R_3=H$ and $R_4=H$; theaflavin monogallate A, which is a compound of the formula (II) with $R_3=3,4,5$-trihydroxy benzoyl group and $R_4=H$; theaflavin monogallate B, which is a compound of the formula (II) with $R_3=H$ and $R_4=3,4,5$-trihydroxy benzoyl group: and theaflavin digallate, which is a compound of the formula (II) with $R_3=3,4,5$-trihydroxy benzoyl group and $R_4=3,4,5$-trihydroxy benzoyl group.

The above described tea polyphenol compounds can be prepared from tea leaves as the starting material and a method for the preparation thereof and a typical example of the product composition are described, for example, in Japanese Patent Kokai 59-219384, 60-13780 and 61-130285, etc.

The anti-dental plaque agent according to the present invention may be added to foodstuffs such as starch jelly, mouth wash, dentifrice and the like by dissolving and mixing the main components or the tea polyphenols directly in and with water, alcohol and the like The concentration may be preferably 100 to 5,000 ppm, more preferably 200 to 1,000 ppm.

Even when added to not only pharmaceuticals but also foodstuffs, the anti-dental plaque agent of the present invention is most unlikely to cause harmful side effects to the human body, since it is chiefly composed of a naturally occurring material or materials drank usually in large amounts. In low concentrations, the present agent is effective against inhibiting the formation of water-insoluble glucan by glucosyltransferase of Streptococcus mutans. Thus, the anti-dental plaque agent of the present invention is very effective for preventing or reducing cariogenesis. The present invention will now be explained specifically but not exclusively with reference to the following example, in which the tea polyphenols used was a green tea extract, a composition containing 30% or more of the catechins (trade name: "Polyphenone 30" made by Mitsui Norin Co., Ltd.) or a green tea extract, a composition containing 90% or more of the catechins (trade name: "Polyphenone 100" made by Mitsui Norin Co., Ltd.) or a black tea extract, a composition containing the theaflavin (trade name "Polyphenone TF" made by Mitsui Norin Co., Ltd.).

EXAMPLE 1

Crude glucosyltransferase was refined from Streptococcus mutans OMZ 176 according to the method described by Mukasa and Slads in Infect. Immun., 8, 555 (1973) and 9, 419 (1974).

The above GTF, labeled sucrose and the anti-dental plaque agent of the present invention were mixed together to the following final concentrations, and was regulated with a 50 mM phosphate buffer (with pH 6.8).

GTF: 0.34 mg protein/ml
0.1 mM (14C) sucrose: 0.1 μCi/μl
Present agent: 1 to 10 mg/ml or 1 to 10 mM.

Twenty (20) μl of the mixture solution were subjected to a reaction for 60 minutes at 37° C. After the completion of the reaction, 5 μl of the reaction mixture and 5 μl of supernatant obtained by centrifugation of the reaction mixture at 5,500×g for 3 minutes were applied to a filter paper respectively, and then developed with a developing solution of butanol-pyridine-water (6:4:3), followed by counting with a scintillation counter. The amount of water-insoluble glucan was found by a difference between the measurements of the reaction mixture and the supernatant. The GTF inhibiting ability is expressed in terms of the rate of inhibiting the formation of water-insoluble glucan with respect to a control to which the antidental plaque agent of the present invention was not added. The results are shown in Tables 1 and 2.

TABLE 1

Effects of Tea Preparations on Water-Insoluble Glucan Formation

| Sample | Concentration (mg/ml) | Inhibition (%) |
|---|---|---|
| Polyphenon 30 | 1.0 | 23 |
|  | 10.0 | 87 |
| Polyphenon 100 | 1.0 | 28 |
|  | 10.0 | 93 |
| Polyphenon B | 1.0 | 21 |
|  | 10.0 | 91 |
| Crude theaflavins | 1.0 | 77 |
|  | 10.0 | 100 |
| Polyphenon-protein complex | 1.0 | 0 |
|  | 10.0 | 19 |

TABLE 2

Effects of Tea Polyphenols on Water-Insoluble Glucan Formation

| Sample | Configuration | Concentration (mM) | Inhibition (%) |
|---|---|---|---|
| (+)-Catechin | 2R,3S | 1.0 | 22 |
|  |  | 10.0 | 62 |
| (−)-Catechin | 2S,3R | 1.0 | 15 |
|  |  | 10.0 | 45 |
| (+)-Epicatechin | 2S,3S | 1.0 | 12 |
|  |  | 10.0 | 42 |
| (−)-Epicatechin | 2R,3R | 1.0 | 5 |
|  |  | 10.0 | 42 |
| (+)-Gallocatechin | 2R,3S | 1.0 | 15 |
|  |  | 10.0 | 51 |
| (−)-Gallocatechin | 2S,3R | 1.0 | 20 |
|  |  | 10.0 | 30 |
| (−)-Epigallocatechin | 2R,3R | 1.0 | 13 |
|  |  | 10.0 | 25 |
| (−)-Epicatechin gallate | 2R,3R | 1.0 | 35 |
|  |  | 10.0 | 83 |
| (−)-Gallocatechin gallate | 2S,3R | 1.0 | 47 |
|  |  | 10.0 | 95 |
| (−)-Epigallocatechin gallate | 2R,3R | 1.0 | 42 |
|  |  | 10.0 | 75 |
| Free theaflavin |  | 1.0 | 57 |
|  |  | 10.0 | 98 |
| Theaflavin monogallate A |  | 1.0 | 64 |
|  |  | 10.0 | 97 |
| Theaflavin monogallate B |  | 1.0 | 47 |
|  |  | 10.0 | 98 |
| Theaflavin digallate |  | 1.0 | 56 |
|  |  | 10.0 | 98 |

We claim:

1. A method of preventing the formation or aggravation of dental plaque consisting essentially of the step of contacting a tooth surface of a patient with at least one tea polyphenol selected from the group consisting of epicatechin gallate, gallocatechin gallate, epigallocatechin gallate, free theaflavin, theaflavin monogallate A, theaflavin monogallante B and theaflavin digallate, said tea polyphenol being in a concentration effective to inhibit the formation and adherence on said tooth surface, of a water insoluble glucan formed by Streptococcus mutans glucosyltransferase.

2. A method for reducing cariogenesis consisting essentially of the step of contacting a tooth surface of a patient with at least one teas polyphenol selected from the group consisting of epicatechin gallate, gallocatechin gallate, epigallocatechin gallate, free theaflavin, theaflavin monogallate A, theaflavin monogallate B and theaflavin digallate, said tea polyphenol being in a concentration effective to inhibit the formation and adherence on said tooth surface, of a water insoluble glucan formed by Streptococcus mutans glucosyltransferase.

3. The method according to claim 1, wherein said tea polyphenol is in a concentration of 100 to 5,000 ppm.

4. The method according to claim 1, wherein said tea polyphenol is in a concentration of 200 to 1,000 ppm.

5. The method according to claim 1, wherein said tea polyphenol is contained in a black tea extract comprising a theaflavin.

6. The method according to claim 2, wherein said tea polyphenol is in a concentration of 100 to 5,000 ppm.

7. The method according to claim 2, wherein said tea polyphenol is in a concentration of 200 to 1,000 ppm.

8. The method according to claim 2, wherein said tea polyphenol is contained in a black tea extract comprising a theaflavin.

* * * * *